US005882497A

United States Patent [19]

Persaud et al.

[11] Patent Number: 5,882,497

[45] Date of Patent: Mar. 16, 1999

[54] SEMICONDUCTING ORGANIC POLYMERS FOR GAS SENSORS

[75] Inventors: Krishna C. Persaud, Manchester, United Kingdom; Paolo Pelosi, Pisa, Italy

[73] Assignee: Aromascan PLC, United Kingdom

[21] Appl. No.: 765,484

[22] PCT Filed: Jun. 20, 1995

[86] PCT No.: PCT/GB95/01449

§ 371 Date: May 19, 1997

§ 102(e) Date: May 19, 1997

[87] PCT Pub. No.: WO96/00383

PCT Pub. Date: Jan. 4, 1996

[30] Foreign Application Priority Data

Jun. 23, 1994 [GB] United Kingdom .................. 9412633

[51] Int. Cl.[6] ............................ C23C 28/00; C25D 5/02; C25D 5/34

[52] U.S. Cl. ......................... 205/188; 205/122; 205/210; 427/255.6

[58] Field of Search .................................. 205/162, 165, 205/188, 122, 210; 427/255.6

[56] References Cited

U.S. PATENT DOCUMENTS

| | | | |
|---|---|---|---|
| 4,696,835 | 9/1987 | Maus et al. | 427/255.6 |
| 4,721,601 | 1/1988 | Wrighton et al. | 422/68 |
| 4,780,796 | 10/1988 | Fukuda et al. | 361/433 |
| 5,017,272 | 5/1991 | Kamigawa et al. | 204/56.1 |
| 5,200,051 | 4/1993 | Cozzette et al. | 204/403 |

FOREIGN PATENT DOCUMENTS

| | | | |
|---|---|---|---|
| 0183047 | 6/1986 | European Pat. Off. . | |
| 0588721 | 3/1994 | European Pat. Off. | 21/320 |
| 2203553 | 9/1990 | United Kingdom . | |
| 8601599 | 3/1986 | WIPO | 27/12 |

OTHER PUBLICATIONS

*B. A. Gregory, "An Introduction to Electrical Instrumentation and Measurement Systems", 1982 (MacMillen) No month available.

*Maisik et al., JCS Faraday Trans. 1, 1986 82, 1117–26 No month available.

*Primary Examiner*—Kathryn Gorgos
*Assistant Examiner*—Edna Wong
*Attorney, Agent, or Firm*—Christie, Parker & Hale, LLP

[57] ABSTRACT

Described is a method of depositing multilayers of semiconducting organic polymers. The method involves polymerising one layer by exposing an oxidising agent to a vapour containing the monomer and polymerising another layer of semiconducting organic polymer electrochemically.

13 Claims, 2 Drawing Sheets

62 66 60 64

SEMICONDUCTING ORGANIC POLYMERS FOR GAS SENSORS

BACKGROUND OF THE INVENTION

This invention relates to a method of depositing multi-layers of semiconducting organic polymers.

Gas sensors based on the use of chemically sensitive semiconducting organic polymers are well known. GB-2, 203,553-B describes a class of gas sensor which consists of two electrodes and a layer of semi-conducting organic polymer deposited on and between the electrodes such as to effect a semiconducting electrical connection. The electrical properties of the semiconducting organic polymer are affected by the presence of a gas or volatile species, and therefore the presence of a gaseous species may be detected by monitoring the change in an electrical property on exposure of the gas sensor to the gas. GB-2,203,553-B discloses the application of an AC electric signal across the gas sensor and the detection of various impedance characteristics, such as conductance. Maisik et al (Maisik, JJ, Hooper, A and Tofield, BC) JCS Faraday Trans. 1, 1986, 82, 1117–26 discloses a gas sensor wherein a DC electric signal is applied, and the DC resistance is detected.

In previous reports of semiconducting organic polymer based gas sensors the polymer has been deposited by electrochemical polymerisation of a solution containing the monomer and a counter-ion.

A major problem with gas sensors which employ a single semiconducting organic polymer to bridge a pair of electrodes is a lack of sensitivity. In general, a large gap between the electrodes is desirable ("large" in this context being greater than ca. 100 um) since experimental evidence shows that a large surface area of polymer can result in enhanced sensitivity. A large surface area of polymer also results in a range of resistances that are easily measurable. However, in practice, the maximum spacing between the electrodes (determined essentially by the length of the polymeric chains) is typically between 1 and 5 um. Wider spacings may be achieved, but at the expense of sensor performance, since, as the electrode spacing increases much beyond the length of the polymeric chains, various mechanical properties worsen and the resistance of the polymer increases dramatically—sometimes prohibitively so. The poor mechanical properties are due to a "necking" effect in the polymer deposit. This effect is illustrated in FIGS. 1 and 2 by reference to a gas sensor with a large separation between the electrodes 10*a* and 10*b*. The electrodes are supported by a substrate 12, and the semiconducting organic polymer 14 has been deposited electrochemically in an uneven manner, with "necking" apparent, both in a plan and a cross-sectional view. Gas sensors of this type are often very brittle and production of the gas sensor suffers from poor reproducibility. Thus International Application No. 93/03355 limits the scope of the multiple gas sensor device claimed to one in which the electrodes are spaced up to 25 um apart, and U.S. Pat. No. 4,721,601 discloses a microelectronic device comprising at least two electrodes separated by less than 2 um.

International Application No. 86/01599 discloses the use of more than one semiconducting organic polymer in a single gas sensor, wherein polypyrrole is employed as a substrate upon which another semiconducting organic polymer is deposited as a coating. Both of these semiconducting organic polymers are polymerised electrochemically. Using such a method, a gas sensor was produced which employed two platinum wire electrodes spaced 200 um apart. However, the electrochemical deposition of the polypyrrole substrate is now found to be not an optimal method, since irrespective of the design of the sensor, the polypyrrole tends to be polymerised as a globule. As a result, the sensor exhibits poor mechanical properties, such as poor adhesion between the polypyrrole and the electrodes, and between the polypyrrole and the second polymer coating. A lack of mechanical robustness is a considerable drawback, since a practical gas sensor should be able to withstand day-to-day usage, including changes in temperature and humidity. Additionally, the adsorption of gaseous species onto the polymer surface (the very process upon which gas detection depends) induces substantial conformational changes in the polymer which can lead to internal stressing.

SUMMARY OF THE INVENTION

According to the present invention there is provided a method for depositing a multilayer of semi-conducting organic polymers wherein the first layer of semiconducting organic polymer is deposited by a vapour phase process which involves exposing an oxidising agent to a vapour containing the monomer, and at least one other layer of polymer is deposited by an electro-chemical polymerisation process. The oxidising agent employed is not limited in scope, but preferred agents comprise ferric chloride, potassium dichromate with sulphuric acid, and potassium ferricyanide.

The multilayer may be deposited onto a device used as a gas sensor which comprises at least one pair of electrodes. In this case, the multilayer is deposited onto and between a pair of electrodes in order to effect a semiconducting electrical connection. The use of a multilayer rather than a single layer of semiconducting organic polymer confers certain advantages which are discussed below. The electrodes of the sensor should be resistent to the electrochemical process employed in the production of the multilayer, and may be carbon or an inert metal such as gold, stainless steel, nickel or platinum.

The spacing between electrodes may be greater than 100 um.

The multilayer may consist of a first layer deposited by the vapour phase chemical oxidation process and a second layer deposited by an electrochemical process. The semiconducting organic polymer deposited by chemical oxidation may be polypyrrole, and prior to the deposition of the multilayer the gas sensor device may be silanated and the substrate surface of the device etched. The oxidising agent may be dissolved in a solvent and applied onto and between pairs of electrodes in the form of a coating. The chemical oxidation process may involve exposing the device to saturated pyrrole and water vapour. The exposure time may be varied in order to control the resistance of the deposited polypyrrole layer and the chemical oxidation process may be carried out at temperatures below −4° C. One particularly useful manifestation of the gas sensor device is a silicon chip carrier wherein the pins of the carrier are used as electrodes, and multilayers of semiconducting organic polymer are deposited between pairs of electrodes. In this instance, the second layer of semiconducting organic polymer may be deposited electrochemically by a method wherein a solution containing the monomer and a counter-ion is dropped into the well of the chip carrier, and a computer controlled potentiostat applies a potential between the selected pair of electrodes and a central cathode.

The present invention provides a superior method for producing a multilayer of semiconducting organic polymers. A substrate layer produced according to the invention adheres well to the electrodes and provides an excellent surface for deposition of a subsequent layer or layers of semiconducting organic polymer. Gas sensors with electrode spacings of 100 um or greater may be readily produced. For example, in the gas sensor device based on a silicon chip carrier the electrode spacing is 300 um. Even this electrode separation should not be considered an upper limit; it is anticipated that gaps as large as several millimetres could be spanned successfully. The chip carrier based multilayer gas sensor is mechanically robust and displays high sensitivity towards gases.

BRIEF DESCRIPTION OF THE DRAWINGS

A multilayer of semiconducting organic polymers in accordance with the invention will now be described with reference to the accompanying drawings, in which.

DETAILED DESCRIPTION

Figure 1:
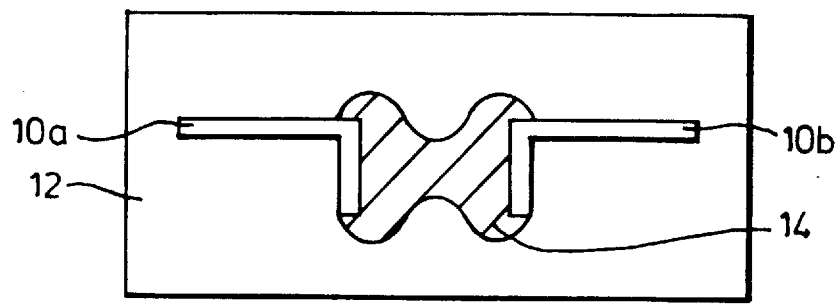
FIG. 1 shows a plan view of a gas sensor showing "necking" of the polymer.
Figure 2:
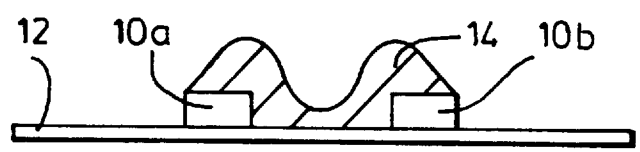
FIG. 2 shows a cross-section of a gas sensor showing "necking" of the polymer.
Figure 3:
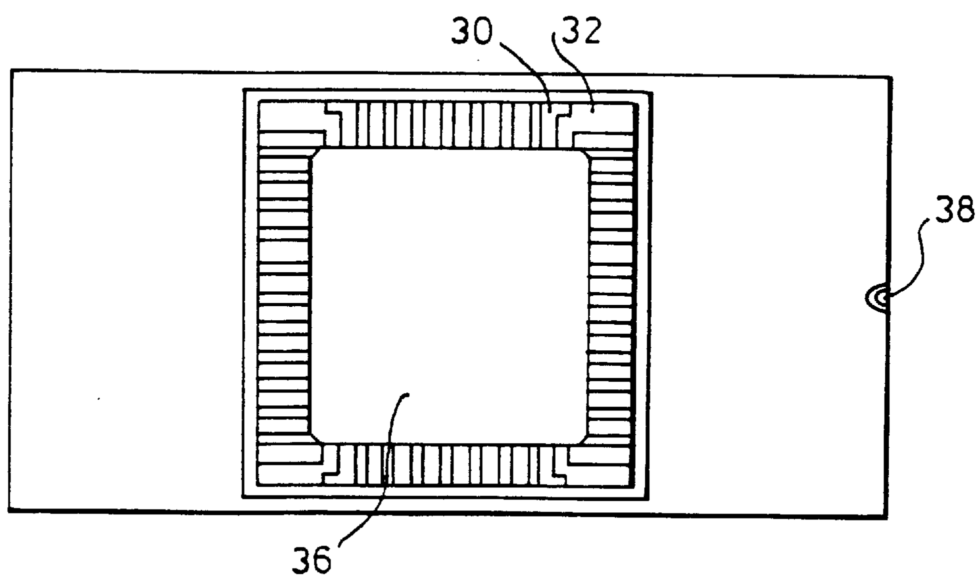
FIG. 3 shows a plan view of a 40 pin silicon chip carrier.
Figure 4:
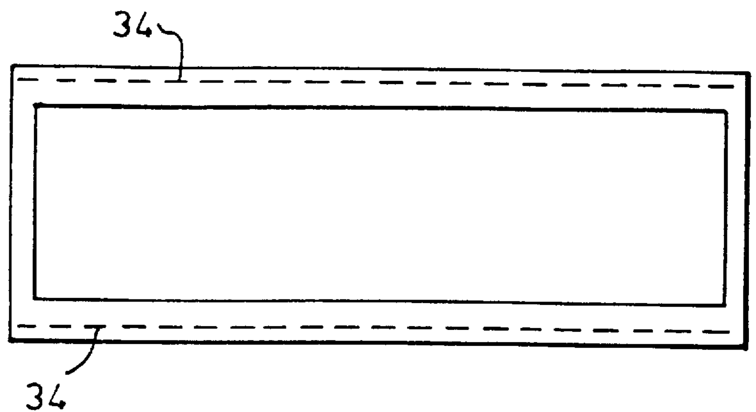
FIG. 4 shows a view from below the 40 pin silicon chip carrier.

Multilayers of semiconducting organic polymers wherein the first layer of polymer is deposited by a vapour phase chemical oxidation process are particularly useful in the production of gas sensors, and one particularly useful form of gas sensor is a modified silicon chip carrier. FIGS. 3 and 4 show a 40 pin silicon chip carrier which comprises gold pins 30 patterned onto a ceramic substrate 32. Voltages may be applied to the pins via connection plugs 34 which are located on the underside of the chip carrier. The central well area 36 may be floated at a user selected potential via connection point 38.

A gas sensor may be fabricated by deposition of a multilayer of semiconducting organic polymer onto and between two adjacent gold pins so that a semiconducting electrical connection between the two pins is affected. The gold pins act as the electrodes of the gas sensor, which may be connected, via the connection plugs, to electrical means and detection means of the types described above. With the 40 pin chip carrier, an array of up to 20 such gas sensors may be produced in a convenient and compact module, and if different multilayers are deposited which exhibit different responses and sensitivities toward different classes of molecule the goal of a multi-purpose gas sensing device may be substantially realised.

In the present embodiment the electrode separation is 300 um, the electrode length is ca. 1,000 um, resulting in a relatively large chemically active sensor surface area of ca. 0.3 $mm^2$ which affords, in consequence, high sensitivity towards gases and odours. It is important to bridge electrodes of this separation with a multilayer of semiconducting organic polymers wherein the first layer of polymer is deposited by a vapour phase oxidative polymerisation process. The resulting gas sensor displays mechanical properties which are superior to those of semiconducting organic polymer based gas sensors produced by previously disclosed methods. In the present, non-limiting, embodiment a bilayer of polymer is deposited, wherein the first layer is polypyrrole. The use of, for instance, further layers of polymer and/or of a different "substrate" layer than polypyrrole is within the scope of the invention.

Prior to polymer deposition, the surface of the chip carrier is rendered hydrophobic by silanation in a soxhlet extractor with a 30% solution of freshly distilled dimethyldichlorosilane in 1,2-dichloroethane for 30 minutes. A drop of chromic acid or like etchant may be placed between each of the 20 alternate pairs of gold pins and left for 2 minutes before washing away with water followed by acetone. The chromic acid treatment etches the ceramic surface of the chip carrier and improves the adhesion of the first layer of deposited polymer.

An oxidising agent is applied onto and between the alternate pairs of electrodes (a pair of electrodes being the two electrodes positioned directly either side of a region of etched ceramic). A suitable oxidising agent is ferric chloride although many other oxidising agents such as potassium dichromate with sulphuric acid and potassium ferricyanide may be employed. A convenient means of application of ferric chloride is to "paint" a 1M solution in 1-methoxy-2-propanol onto the electrodes. The chip carrier is then exposed to saturated pyrrole and water vapour, preferably at temperatures below −4° C., most preferably at temperatures around −20° C. The pyrrole is oxidised by the $Fe^{3+}$ ions to form a thin film of polypyrrole between all twenty of the electrode pairs. Some control over the resistance of the oxidatively deposited polypyrrole film can be exercised by varying the time of exposure. For instance, an exposure time of one minute results in a resistance of ca. 200 ohms, 2 minutes results in 100 ohms and 5 minutes results in 50 ohms. The chip carrier is then washed with acetonitrile, dried, and the resistances of the sensors measured.

Figure 5:
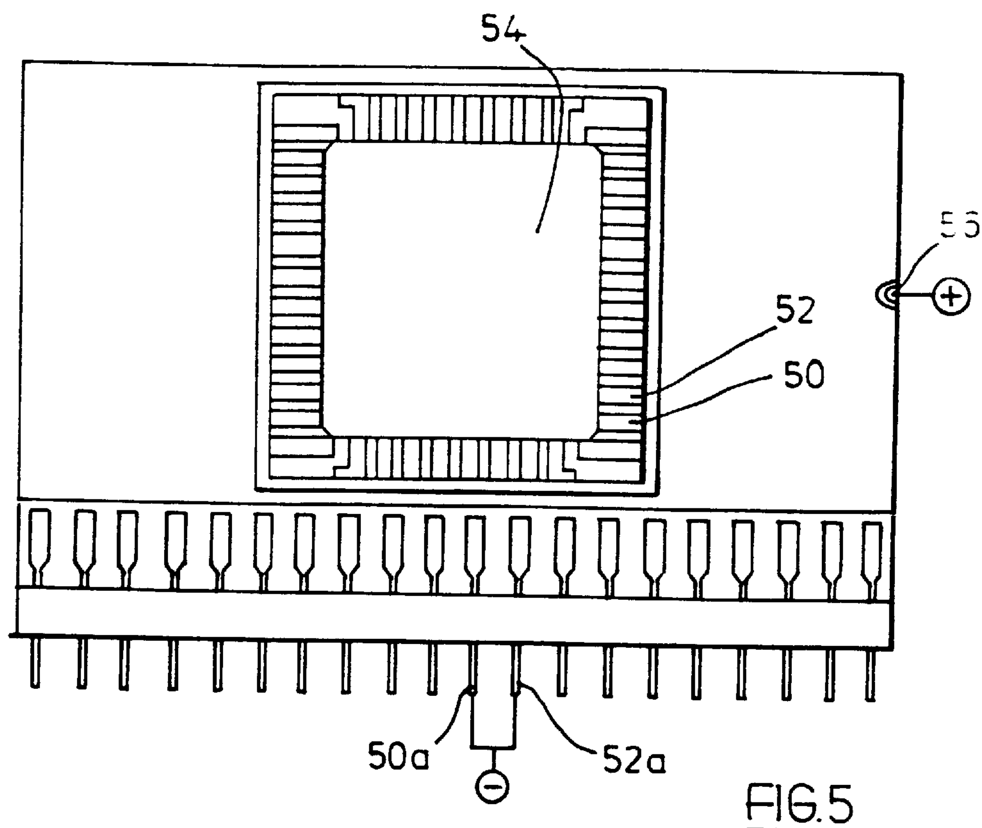
FIG. 5 shows the set-up for electrochemical polymerisation.

The second layer of semiconducting organic is then electrochemically deposited on each polypyrrole sensor individually. FIG. 5 depicts the electro-chemical polymerisation of the sensor defined by electrodes 50 and 52. Approximately 50 ul of a solution containing the monomer and tetraethylammonium p-toluenesulphonate (0.1M) is placed in the central well 54 of the chip carrier. The nature of the solvent and the concentration of monomer depends on the specific monomer used, but typically a 99% acetonitrile/1% water mixture or a 50% dichloromethane/49.5% acetonitrile/0.5% water mixture is employed as a solvent, with the monomer concentration in the range 0.1–0.01M. Electrical connections are made to the electrodes at plugs 50*a* and 52*a*, and to the central well at point 56, so that the electrodes are the anodes and the central well the cathode of an electrical circuit. A computer controlled potentiostat applies a potential between the electrodes and the central cathode and the monomer is polymerised onto the gas sensor surface. Deposition conditions are optimised for the particular monomer employed, but typically a potential difference of 1.3–2.5 V and a deposition time of 15–30 s is used. After each electrochemical deposition the chip carrier is washed with acetonitrile and the process is repeated with the next sensor/monomer combination until an array of 20 gas sensors is fabricated. The array may be subjected to accelerated ageing by calcination at 200° C. for 10–20 minutes, the effect of this treatment being to increase the sensor resistances by approximately an order of magnitude.

Figure 6:
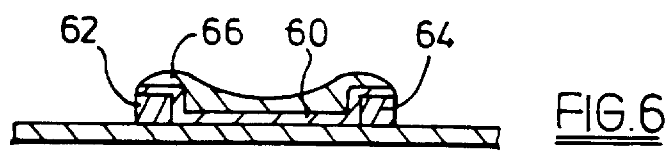
FIG. 6 shows a cross-section of a gas sensor with a multilayer of polymer.

FIG. 6 shows a cross-sectional view through an individual gas sensor and illustrates that the polypyrrole layer 60 is deposited on and between the electrodes 62 and 64 as a regular and smooth film. This film constitutes an excellent substrate layer for the electrochemical deposition of the second polymer layer 66. As a result, a gas sensor is produced which possesses excellent mechanical properties and exhibits long term stability.

We claim:

1. A method for depositing multilayers of different semiconducting organic polymers comprising depositing a layer of semiconducting organic polymer polymerised by exposing an oxidising agent to a vapour containing the monomer to be polymerised and depositing at least one other layer of a different semiconducting organic polymer polymerised electrochemically and wherein the multilayers of semiconducting organic polymer are deposited on a device that includes a substrate surface and is used as a gas sensor and wherein said device contains at least one pair of electrodes and said multilayers are deposited onto and between said pair of electrodes to effect a semiconducting electrical connection.

2. A method according to claim 1, wherein the oxidising agent comprises one of ferric chloride, potassium dichromate with sulphuric acid, or potassium ferricyanide.

3. A method according to claim 1, wherein the electrodes are made of an inert metal or carbon.

4. A method according to claim 1, wherein each pair of electrodes is separated by at least 100 um.

5. A method according to claim 1, wherein the semiconducting organic polymer deposited by oxidation is polypyrrole.

6. A method according to claim 5, wherein said device is silanated and the substrate surface of the device is etched prior to polymer deposition.

7. A method according to claim 1, wherein the oxidising agent for oxidation is dissolved in a solvent and is applied onto and between pairs of electrodes as a coating.

8. A method according to claim 7, wherein the device is exposed to saturated pyrrole and water vapour and wherein the deposited layer comprises polypyrrole and resistance of the deposited layer of polypyrrole is controlled by varying the duration of exposure during the oxidation.

9. A method according to claim 8, wherein the layer of semiconducting organic polymer polymerized by exposing an oxidizing agent to a vapor containing the monomer is carried out at temperatures below −4° C.

10. A method according to claim 1, wherein the device is a silicon chip carrier and said carrier has a well.

11. A method according to claim 10, wherein said at least one other layer is deposited by a method wherein a solution containing a monomer to be polymerized and a counter-ion is placed into the well of the chip carrier and a computer controlled potentiostat applies a potential between a selected pair of electrodes and a central cathode.

12. A method for fabricating a gas sensor having at least one pair of electrodes and multilayers of semiconducting organic polymers deposited onto and between said electrodes in order to effect a semiconducting electrical connection between the electrodes comprising depositing a layer of semiconducting organic polymer polymerised by exposing an oxidising agent to a vapour containing a monomer and depositing another layer of semiconducting organic polymer which is polymerised electrochemically onto and between said electrodes.

13. A method for depositing multilayers of semiconductive organic polymers onto and between at least one pair of electrodes to effect an electrical connection therebetween which comprises depositing a polymer layer polymerised by exposing an oxidising agent to a vapour containing the monomer to be polymerised and depositing another layer of semiconductive organic polymer which is polymerised electrochemically onto and between said electrodes.

* * * * *

UNITED STATES PATENT AND TRADEMARK OFFICE

CERTIFICATE OF CORRRECTION

PATENT NO. : 5,882,497
DATED : March 16, 1999
INVENTOR(S) : Krishna C. Persaud, et al.

It is certified that error appears in the above-identified patent and that said Letters Patent is hereby corrected as shown below:

On the title page, item [56], insert the following:

FOREIGN PATENT OR PUBLISHED FOREIGN PATENT APPLICATION

| | | DOCUMENT NUMBER | | | | | | | PUBLICATION DATE | COUNTRY OR PATENT OFFICE | CLASS | SUBCLASS | TRANSLATION | |
|---|---|---|---|---|---|---|---|---|---|---|---|---|---|---|
| | | | | | | | | | | | | | YES | NO |
| | 3 | 6 | 2 | 1 | 7 | | | | 01/1991 | Japan | | | | |
| | | | | | | | | | | | | | | |

Signed and Sealed this

Twenty-sixth Day of October, 1999

Attest:

Q. TODD DICKINSON

*Attesting Officer* — *Acting Commissioner of Patents and Trademarks*